United States Patent [19]
Bays et al.

[11] Patent Number: 4,976,715
[45] Date of Patent: Dec. 11, 1990

[54] REPAIR TACK FOR BODILY TISSUE

[75] Inventors: F. Barry Bays, Seminole; Arthur F. Trott, Largo; Sam R. Marchand, Dunedin, all of Fla.

[73] Assignee: Concept, Inc., Largo, Fla.

[21] Appl. No.: 472,298

[22] Filed: Jan. 30, 1990

Related U.S. Application Data

[63] Continuation of Ser. No. 195,417, May 16, 1988, Pat. No. 4,924,865, which is a continuation of Ser. No. 865,184, May 20, 1986, abandoned.

[51] Int. Cl.$^5$ .................... A61B 17/00; F16B 35/00
[52] U.S. Cl. .................... 606/77; 606/220; 411/392; 411/395; 411/510
[58] Field of Search ............ 411/392, 395, 510, 358; 606/77, 213, 219, 220

[56] References Cited

U.S. PATENT DOCUMENTS

| | | | |
|---|---|---|---|
| 4,060,089 | 11/1977 | Noiles | 606/220 |
| 4,507,817 | 4/1985 | Staffeld | 411/395 |
| 4,532,926 | 8/1985 | O'Holla | 606/330 |
| 4,873,976 | 10/1989 | Schreiber | 606/213 |

*Primary Examiner*—Randall L. Green
*Assistant Examiner*—Gary Jackson
*Attorney, Agent, or Firm*—Epstein, Edell & Retzer

[57] ABSTRACT

An apparatus for repairing in vivo torn cartilaginous or other bodily tissue, particularly torn meniscus tissue during arthroscopic surgery, employs a repair tack of biodegradable material chosen to have a degradation time in excess of the required healing time for the tissue. The repair tack has a shaft portion with a longitudinal bore and a grip portion adapted for releasable engagement by a hollow applicator. In one embodiment the grip portion of the tack is a cross bar, at the proximal end of the shaft, which fits into an open-sided slot at the forward end of the applicator.

14 Claims, 1 Drawing Sheet

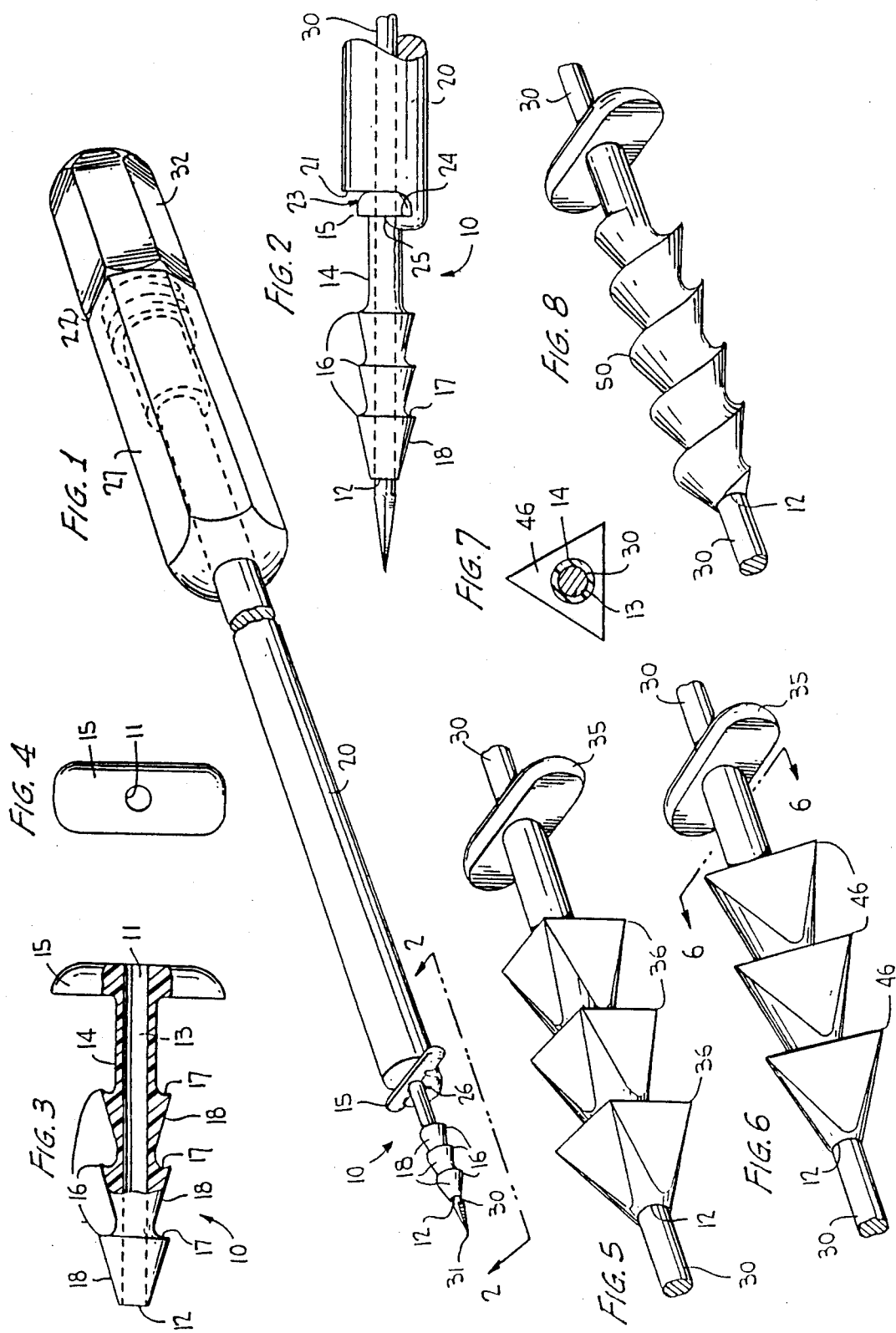

REPAIR TACK FOR BODILY TISSUE

This application is a continuation of application Serial No. 07/195,417 filed May 16, 1988 which is a continuation of application Serial No. 06/865,184 filed May 20, 1986, now abandoned.

BACKGROUND OF THE INVENTION

1. Technical Field

The present invention relates to apparatus for repairing bodily tissue in vivo and has particular utilization in repairing a meniscal tear during arthroscopic surgery of the knee.

2. Discussion of the Prior Art

Although the following description is directed specifically to repairing meniscus tissue in vivo in a human knee, it should be understood that the principles of the present invention are applicable to the repair of any bodily tissue, such as cartilage, bone, skin and ligaments, in an in vivo surgical procedure.

The knee is a hinge joint which permits a limited amount of rotation. The opposing curvature of the articulating surfaces of the femur and tibia are equalized, to a certain degree, by the menisci, the wedge-shaped fibrocartilaginous structures located on the periphery of the articular surface. The menisci are mobile buffers functioning to inhibit displacement of the joint and to distribute the force exerted by the femur over a larger area of the tibia. Possible causes of damage or injury to the menisci are multiple. Damage or tear of a meniscus usually occurs when the weight-bearing joint is subjected to a combined flexion-rotation or extension-rotation motion. The elastic and fibrous structure of the menisci, the rigid fixation of the anterior and posterior attachments, and their connections with the joint capsule, cause the menisci to return to their normal positions at the periphery of the joint if there is displacement. Disturbance of the normal mechanism of the joint and interference with mobility of the menisci can exceed their elasticity and cause tears of the cartilaginous substance. This appears to occur most frequently when a meniscus that has been displaced into the joint is caught between the femoral and tibial condyles as the result of a sudden change of movement.

Treatment for torn menisci has changed considerably over the years. At one time it was advocated that a peripherally detached meniscus be removed, even though the tissue was not damaged. The rationale was that excision of the meniscus prevents meniscal re-injury in a joint in which the mechanics may have been disturbed. In many cases a complete meniscectomy (i.e., total removal of the meniscus) was performed. Results from a complete meniscectomy ultimately showed degenerative arthritis, instability and changes in the transmission of loads in the knee. Because of these complications a partial meniscectomy became an alternative to a complete meniscectomy. Recently, there has been a strong movement to save as much of the meniscus as possible, leading to the development of techniques for meniscal suturing. Animal studies have been performed to demonstrate the safety and efficiency for this procedure.

An arthrotomy, or open technique, requires large incisions to gain access to the joint. Utilizing the open technique for meniscal suturing repair provided the opportunity of returning the knee to its prior pre-injury level of performance; however, the resulting large incisions require longer periods of immobilization and consequently longer periods of rehabilitation and recovery. Recent advances in instrumentation have made it possible to repair some meniscal lesions under arthroscopic visualization. Generally, this instrumentation is for inserting and receiving the suture as it passes through the meniscus. Typically, suture is passed through the meniscal rim and body of the meniscus, guided by special cannulas through the knee. The suture is then tied posterior to the knee and placed subcutaneously. Most of these procedures are performed using a larger (i.e., four to eight centimeters) incision than the standard portals used in arthroscopy. Depending upon the meniscus to be repaired, the incision is placed on the medial or lateral side of the knee; however, because of the long needles generally employed in meniscal repair, extreme caution must be observed during this procedure in order to avoid the possibility of the needle penetrating the popliteal artery or posterior tibial nerve and catching the fat pad during passage of the needle into and out of the knee joint. A spoon-shaped instrument is generally employed to act as a needle shield or guard for the popliteal structures. Nevertheless, there have been reported instances of injury to these vital areas with consequential damage to arteries and nerve palsy in the limb. Surgical techniques are being perfected, as are improvements to instrumentation, by various groups in order to minimize these risks and to decrease the procedural time.

It is known to use certain types of metal staples in conjunction with surgery for repairing bone tissue. The legs or shafts of the staple have a series of barbs which hold the staple and surrounding base tissue in place during the healing process. Another known device serving a similar function is the Smillie nail which is a single shaft device employed for securing bone tissue parts in place during the healing process. These staple and nail devices are effective for holding the bone tissue together during healing; however, they require a second surgical procedure in order to remove the device after the tissue has healed.

OBJECTS AND SUMMARY OF THE INVENTION

It is therefore an object of the present invention to provide an apparatus for repairing bodily tissue in vivo requiring only a single surgical procedure and a small incision.

It is another object of the present invention to provide an apparatus for healing torn or severed tissue, particularly meniscus tissue, using a safer surgical procedure than is currently employed.

A further object of the present invention is to provide an apparatus for healing torn or severed bodily tissue with a single surgical procedure requiring far less time than the procedure currently employed.

In accordance with the present invention a repair tack is designed for surgical utilization, particularly in arthroscopic surgery, to repair a torn meniscus, the tack being generally T-shaped with a hollow stem. Along the outer surface of the stem there are a plurality of barbs. An applicator for the repair tack includes a tack holder having a slot for receiving the cross bar of the T-shaped tack and further includes a needle passing through an axial opening in the applicator and through the axial bore in the stem of the tack. With the tack supported in the slot and the needle passing through the stem, the applicator and the tack can be inserted into the joint cavity through a portal in the skin or through an insertion cannula. The sharpened point of the needle is placed in contact with the torn meniscus portions (or other severed tissue) and force is applied to the holder and needle to cause the needle and tack to penetrate those meniscus portions to a desired depth. The point of the needle is then withdrawn into the axial opening of the applicator and the cross bar of the tack is displaced from the slot leaving the tack firmly secured in the meniscus. The tack is made from a biodegradable polymer or copolymer selected in accordance with desired degradation time and anticipated time for healing the torn meniscus.

The tack performs a function similar to that of biodegradable suture presently employed in meniscal and other surgical repair. It is safer than utilizing suture because it penetrates only the meniscus and does not enter the popliteal space. The risk in reaching and possibly damaging the vital areas in the posterior section of the knee is greatly reduced. The tack device holds the torn meniscal sections in apposition while the tissue regenerates and healing is effected. In addition, the time required for placement of the tack device is much shorter than that required to place the suture. Consequently, the total procedural time is shortened, thereby decreasing the time during which a tourniquet must be utilized to restrict blood flow to the limb. Thus, reduced risk of possible damage to the vital area in the back of the knee, and reduced tourniquet time, are primary advantages of the tack device.

The repair tack is formed from an absorbable polymer or copolymer, preferably derived from glycolic and lactic acids. It is a synthetic polyester chemically similar to other commercially available glycolide/lactide copolymers. In vivo, glycolide and lactide degrade and absorb by hydrolysis to lactic acid and glycolic acid which are then metabolized by the body. The combination of glycolide and lactide has been used for many years in suturing material.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 1 is a view in perspective of a repair tack, applicator and insertion needle of the present invention;

FIG. 2 is a detailed side view in elevation of the forward end of the apparatus of FIG. 1;

FIG. 3 is a top view in plan and partial section of the tack device of the apparatus of FIG. 1;

FIG. 4 is an end view in elevation of the tack device of FIG.3;

FIG. 5 is a view in perspective of an alternative embodiment of the tack device employed with the apparatus of FIG. 1;

FIG. 6 is a view in perspective of still another embodiment of the tack device of the present invention;

FIG. 7 is a view in section taken along lines 6—6 of FIG. 6; and

FIG. 8 is a view in perspective of a further embodiment of the tack device of the present invention.

DESCRIPTION OF THE PREFERRED EMBODIMENTS

Referring specifically to FIGS. 1-4 of the accompanying drawings, a preferred embodiment of the present invention takes the form of a repair tack 10 for deployment in torn cartilage or other bodily tissue, in vivo, by means of an applicator 20 and needle 30. The repair tack 10 is preferably fabricated as an integrally molded unit from suitable rigid or semi-rigid biodegradable plastic material chosen in accordance with considerations described hereinbelow. It should also be noted that the tack may be formed by means of any suitable process, such as machining. Proximal nd distal ends of the tack are designated by reference numerals 11 and 12, respectively, and are joined by a substantially cylindrical bore 13 extending axially (i.e., longitudinally) through the entire length of the tack 10. Most of that length is occupied by a shaft portion 14 extending rearwardly from distal end 12 to join a flange-like cross bar grip portion 15 disposed at proximal end 11. Grip portion 15, in the embodiment of FIGS. 1-4, takes the form of a generally rectangular parallelepiped with rounded corners and having its longest dimension extending transversely with respect to the axis of shaft 14 and internal bore 13. As is clearly illustrated in FIG. 3, bore 3 extends perpendicularly through the cross bar grip portion 15 and axially through shaft portion 14.

The shaft portion 14 is substantially cylindrical, with bore 13 disposed coaxially therein, and includes a plurality of barb members 16 disposed in axial sequence along its periphery. In the preferred embodiment the barb members 16 are frusto-conical in configuration, widening in diameter in a direction from distal end 12 toward proximal end 11. The distal barb tapers to terminate at a sharp circular edge at distal end 12 of the shaft. The resulting tapered surface 18 of the barb members 16 facilitates passage of the shaft portion 14 of tack member 10 through cartilaginous or other tissue when the tack is moved forwardly (i.e., in a direction along the axes of shaft portion 14 and bore 13 from proximal end 11 toward distal end 12). The rearward facing surface 17 of each barb member 16 intersects the large diameter end of tapered surface 18 and includes an annular section disposed in a plane oriented substantially perpendicular to the axes of bore 13 and shaft portion 14. This perpendicular orientation is not crucial for the resent invention; rather, what is important is that surface 17 be oriented to preclude rearward movement and resulting inadvertent removal of the tack member 10 from cartilaginous or other tissue into which the tack member has been deployed. In this regard, it is important that surface 17 not be tapered to any significant degree in the opposite direction to the taper of surface 18. In the preferred embodiment of the invention there are three barb members 16 disposed in successive axial adjacency with the most remote barb member having its narrow diameter end terminating at distal end 12. Approximately one-third of the length of shaft portion 14 remains between the rearmost barb member 16 and crossbar grip portion 15 and has a smooth cylindrical configuration. As few as one and more than three barb members may be provided within the scope of the present invention, so long as the barb member or members provide sufficient resistance to rearward movement of the shaft portion through the cartilaginous tissue.

Applicator 20 is an elongated hollow cylindrical member having a forward end 21 adapted for attachment to tack member 10 and a rearward end 22 from which deployment of the tack member is controlled. The hollow interior of applicator 20 may take the form of an axial bore suitable for receiving needle 30 in axially slidable engagement. Forward end 21 of applicator 20, when viewed from the side, has a generally J-shaped configuration to define a slot 23 for receiving the crossbar grip portion 15 of tack member 10. Specifically, slot 23 has an interior surface 24 contoured to match the contour of grip portion 15 and is open along one side to permit easy insertion and removal of the grip portion. A forward lip 25 extends across the slot 23 terminating the short leg of the J-configuration and serves to restrain the grip portion 15 of tack member 10, when it is in slot 23, against axial movement (i.e., longitudinally of applicator 20 and tack member 10) and against twisting or rotation about any axis extending vertically (as viewed in FIG. 2). A cut-out portion 26 in lip 25 receives and supports the rearmost end of the shaft portion 14 of the tack member and, along with needle 30, precludes movement of grip portion 15 along its axis transversely of shaft portion 14.

Needle 30 has a sharp end 31 and a rearward end 32 and is sufficiently long to extend entirely) through applicator 20 and tack member 10 such that pointed end 31 extends forwardly of the distal end 12 of the tack member. The bores defined in applicator 20 and tack member 10 are sized to permit slidable movement of the needle within these members. Rearward end 32 of needle 30 includes an enlarged handle part which can be grasped between a surgeon's thumb and forefinger so that the needle can be pushed forwardly into and pulled rearwardly from cartilaginous tissue. The needle is preferably made from stainless steel and is secured, at its rearward end, to a threaded male connector adapted to engage a threaded female connector 27 at the rearward end of applicator 20. The applicator is preferably made from a suitably machined or molded metal mate Tack member 10 is made from a biodegradable polymer or copolymer of a type selected in accordance with the desired degradation time. That time, in turn, depends upon the anticipated healing time for the cartilaginous or other tissue which is the subject of the surgical procedure. Known biodegradable polymers and copolymers range in degradation time from about three months for polyglycolide to about forty-eight months for polyglutmic-co-leucine. A common biodegradable polymer used in absorbable sutures and the like is poly(L-lactide) which has a degradation time of about twelve to eighteen months.

As discussed briefly above the actual material used for tack member 10 is preferably an absorbable copolymer derived from glycolic and lactic acids, such as a synthetic polyester chemically similar to other commercial available glycolide and lactide copolymers. Glycolide and lactide, in vivo, degrade and absorb by hydrolysis into lactic acid and glycolic acid which are then metabolized by the body.

The table set forth below lists polymers (and copolymers and terpolymers thereof) which are useful for the biodegradable material employed for the tack member 10 of the present invention. These polymers are all biodegradable into water-soluble non-toxic materials which can be eliminated by the body. All are well known for use in humans and their safety has been demonstrated and approved by the U.S. Food and Drug Administration. Although these polymers are normally linear, cross linked resins can be prepared from these materials by those skilled in the art.

TABLE

| Polymer |
| --- |
| Polycaprolactone |
| Poly(L-lactide) |
| Poly(DL-lactide) |
| Polyglycolide |
| 95:5 Poly(DL-lactide-co-glycolide) |
| 90:10 Poly(DL-lactide-co-glycolide) |
| 85:15 Poly(DL-lactide-co-glycolide) |
| 75:25 Poly(DL-lactide-co-glycolide) |
| 50:50 Poly(DL-lactide-co-glycolide) |
| 90:10 Poly(DL-lactide-co-caprolactone) |
| 75:25 Poly(DL-lactide-co-caprolactone) |
| 50:50 Poly(DL-lactide-co-caprolactone) |
| Polydioxanone |
| Polyesteramides |
| Copolyoxalates |
| Polycarbonates |
| Poly(glutamic-co-leucine) |

The repair tack 10 illustrated in the accompanying drawings is primarily intended for use in arthroscopic surgery for the repair of torn meniscus tissue; however, it also has utilization for repairing other bodily tissue. The apparatus illustrated in FIG. 1 is assembled, prior to insertion into the body joint, by placing the cross bar portion 15 into slot 23 at the forward end of applicator 20. Needle 30 is then slidably passed through the hollow applicator and bore 13 in tack member 10, and threaded connectors 27 and 32 are tightened. With the tack member firmly supported in slot 23 and by needle 30, the device may be inserted into the joint cavity where the meniscus repair is to take place through a suitable portal in the skin or through an insertion cannula.

In order to apply the tack to the torn cartilaginous tissue, the sharpened point 31 of the needle is placed into contact with the tissue and force is applied to the applicator and needle 30 (locked together by the above-described threaded engagement) to cause the needle and tack to penetrate the torn meniscus portions to the desired depth. The connectors 27 and 32 are disengaged and the sharpened point 31 of the needle is then withdrawn from the tack member 10 into the applicator 20. Cross bar grip portion 15 may then be removed from slot 23 by rotating the forward end of applicator 20 downwardly (i.e., downwardly as viewed in FIG. 2), transversely of the axis of bore 13. Applicator 20 may then be withdrawn away from the tack, leaving the tack 10 firmly secured within the torn meniscus portions in a position to retain the torn portions in close proximity. As noted above, the tack dissolves over a period of time sufficient to permit healing of the torn meniscus tissue.

As illustrated in FIG. 5, 6, 7 and 8, the barb members on the tack need not be limited to a frusto-conical configuration, nor must the grip portion be cylindrical. Any barb and grip portion configuration consistent with the functions described herein may be employed. Thus, the tack member illustrated in FIG. 5 is provided with barb members 36 having a truncated pyramidal configuration with a substantially square or other rectangular transverse cross section. The embodiment of FIGS. 6 and 7 includes barb members 46 which are truncated pyramids having a triangular transverse cross section. In both of these embodiments, the grip 35 takes the form of a rectangular parallelepiped. In the embodiment of FIG. 8 the "barbs" are actually a continuous helical barb 50 extending about the shaft periphery for a portion of the shaft length.

As noted above, the tack member 10 is ideally suited for holding torn meniscus tissue in place while the tissue heals. By way of example only, a suitable set of dimensions for tack member 10 of FIGS. 1-3 would be as follows: the overall length from proximal end 11 to distal end 12: 0.345 inch; the axial length of the distal barb member: 0.075 inch; the axial length of the other barb members: 0.06 inch; the diameter of each barb member at its widest end: 0.065 inch; the diameter of bore 13: 0.025 inch; overall length of cross bar grip portion 15 in the dimension extending transversely of bore 13 and radially symmetrically thereabout: 0.175 inch; thickness of cross bar grip portion 15 parallel to the axis of bore 13: 0.025 inch; and angle of surface 18 relative to axis of bore 13: 14°. It is to be understood, of course, that variations from these dimensions are possible for different utilizations of tack member 10.

The positioning of bore 13 of tack member 10 along the axial center line of the tack member is advantageous in that it permits the insertion needle to stabilize the tack and provide a means for penetrating the tissue.

From the foregoing description it will be appreciated that the invention makes available a novel method and apparatus for healing torn cartilaginous tissue, in vivo, in a manner which requires a single surgical procedure utilizing a minimal amount of time and a relatively small incision.

Having described the preferred embodiment of a new and improved repair tack for cartilaginous tissue and in vivo method of deploying same in accordance with the present invention, it is believed that other modifications, variations and changes will be suggested to those skilled in the art in view of the teachings set forth herein. It is therefore to be understood that all such variations, modifications and changes are believed to fall within the scope of the present invention as defined by the appended claims.

We claim:

1. A tack for holding together tissue to permit healing in vivo comprising
    a shaft having a proximal end, a distal end and a substantially cylindrical bore extending longitudinally from said proximal end to said distal end to allow a needle to pass freely entirely through said shaft to extend from said distal end for penetration in the tissue; and
    a plurality of barbs disposed along said shaft, said barbs including a distal barb tapering to terminate at a sharp circular edge at said distal end of said shaft, said sharp circular edge having a diameter substantially the same as said bore to facilitate penetration and imbedding of said barbs in the tissue,
    entirely of said tack being made of a biodegradable material having a degradation time selected to be at least as long as the required healing time for the tissue.

2. A tack as recited in claim 1 wherein said distal barb has an axial length greater than the axial length of the other barbs.

3. A tack as recited in claim 1 wherein said barbs have rear surfaces facing said proximal end and disposed substantially perpendicular to the longitudinal dimension of said shaft.

4. A tack as recited in claim 1 wherein said barbs each have a frusto-conical configuration.

5. A tack as recited in claim 1 wherein said barbs each have a truncated pyramidal configuration.

6. A tack as recited in claim 5 wherein said barbs has a generally rectangular transverse cross-section.

7. A tack as recited in claim 1 wherein each of said barbs has a generally rectangular transverse cross-section.

8. A tack as recited in claim 1 wherein the tack in its entirety is an integrally-molded plastic unit.

9. A tack as recited in claim 1 wherein said barbs are formed of a continuous helical barb extending about said shaft over a portion of the length of said shaft.

10. A tack for holding tissue to permit healing in vivo comprising
    a shaft having a proximal end, a distal end and a bore extending longitudinally through said shaft from said proximal end to said distal end for allowing a needle to pass through said shaft to extend from said distal end for penetrating the tissue; and
    a distal barb terminating at a sharp circular edge at said distal end of said shaft, said sharp circular edge having a diameter substantially the same as said bore to facilitate penetration and imbedding of said barb in the tissue.

11. A tack as recited in claim 10 wherein the entirety of said tack is made of a biodegradable material.

12. A tack as recited in claim 11 and further comprising at least one additional barb disposed on said shaft between said distal barb and said proximal end.

13. A tack as recited in claim 10 and further comprising at least one additional barb disposed on said shaft between said distal barb and said proximal end.

14. A tack for insertion in the body to hold tissue for healing comprising
    a shaft having a proximal end and a distal end with a bore extending longitudinally through said shaft from said proximal end to said distal end, said distal end having a sharp circular edge of substantially the same diameter as said bore,
    the entirety of said tack being made of biodegradable material as an integral unit.

* * * * *

UNITED STATES PATENT AND TRADEMARK OFFICE
CERTIFICATE OF CORRECTION

PATENT NO. : 4,976,715
DATED : December 11, 1990
INVENTOR(S) : F. Barry Bays et al It is certified that error appears in the above-identified patent and that said Letters Patent is hereby corrected as shown below:

Column 4, line 14, delete "nd" and replace with --and--;

line 26, delete "3" and replace with --13--;

line 47, delete "resent" and replace with --present--;

Column 5, line 24, the parenthesis after "entirely" should be deleted;

line 39, delete "mate" and replace with --material--;

line 52, after "above" insert a --,--;

Column 6, line 67, delete "periphary" and replace with --periphery--;

Column 7, line 53, delete "entirely" and replace with --the entirety--.

Signed and Sealed this

Twenty-sixth Day of May, 1992

Attest:

DOUGLAS B. COMER

*Attesting Officer*     Acting Commissioner of Patents and Trademarks